United States Patent [19]
Asai et al.

[11] Patent Number: 5,996,903
[45] Date of Patent: Dec. 7, 1999

[54] ATOMIZER AND ATOMIZING METHOD UTILIZING SURFACE ACOUSTIC WAVE

[75] Inventors: Kei Asai; Takanobu Yamauchi, both of Kyoto, Japan

[73] Assignee: OMRON Corporation, Kyoto, Japan

[21] Appl. No.: 09/000,299

[22] PCT Filed: Aug. 5, 1996

[86] PCT No.: PCT/JP96/02209

§ 371 Date: Jan. 27, 1998

§ 102(e) Date: Jan. 27, 1998

[87] PCT Pub. No.: WO97/05960

PCT Pub. Date: Feb. 20, 1997

[30] Foreign Application Priority Data

Aug. 7, 1995 [JP] Japan .................................. 7-200769

[51] Int. Cl.$^6$ .................................................. B05B 17/04
[52] U.S. Cl. .............................. 239/4; 239/4; 239/102.1; 239/102.2; 222/409
[58] Field of Search ............................. 239/102.1, 102.2; 222/409

[56] References Cited

U.S. PATENT DOCUMENTS

| | | | |
|---|---|---|---|
| 5,297,734 | 3/1994 | Toda | 239/102.2 |
| 5,299,739 | 4/1994 | Takahashi et al. | 239/102.2 |
| 5,657,926 | 8/1997 | Toda | 239/102.2 |

FOREIGN PATENT DOCUMENTS

| | | |
|---|---|---|
| 03232562 | 10/1991 | Japan . |
| 04349961 | 4/1992 | Japan . |
| 08052216 | 2/1996 | Japan . |

OTHER PUBLICATIONS

Surface Acoustic Wave Atomizer with Pumping Effect, Minoru Kurosawa et al., Proceedings of 8$^{th}$ IEEE International Workshop on Micro Electrictro Mechanical Systems, Jan. 30–Feb. 2, 1995, Amsterdam, The Netherlands, pp: 1–6.

*Primary Examiner*—Kevin P. Shaver
*Assistant Examiner*—David Deal
*Attorney, Agent, or Firm*—Morrison & Foerster LLP

[57] ABSTRACT

An ultrasonic atomizer utilizing surface acoustic waves is disclosed. The atomizer comprises an oscillator (11) generating surface acoustic waves, and a porous thin plate (12a) having a number of through holes arranged on n oscillating surface of the oscillator with a small clearance. A liquid (19) in a liquid container (18) is aspirated into the small clearance part between the oscillator and the porous thin plate by vibration by the surface acoustic waves or by capillarity. Vibration of the surface acoustic waves is transmitted to the porous thin plate (12a) through the liquid in the small clearance part, and a small quantity of liquid penetrating into holes of this thin plate is atomized by the vibration and sprayed to the exterior. According to this atomizer, it is possible to perform atomization by employing a battery of small power, and the balance between the supply quantity of the liquid and the atomization quantity can be kept excellent.

14 Claims, 11 Drawing Sheets

BLOCK DIAGRAM OF EMBODIMENT OF SURFACE ACOUSTIC WAVE ATOMIZER

ATOMIZER AND ATOMIZING METHOD UTILIZING SURFACE ACOUSTIC WAVE

TECHNICAL FIELD

The present invention relates to an atomizer and an atomizing method utilizing surface acoustic waves, and more particularly, it relates to an ultrasonic atomizer used for cure of asthma or pulmonary diseases.

BACKGROUND TECHNIQUE

An atomizer employing surface acoustic waves is described in "Surface Acoustic Wave Atomizer with Pumping Effect" of Proceedings of $8^{th}$ IEEE International Workshop on Micro Electrictro Mechanical Systems 30 Jan.–2 February 1995 Amsterdam, The Netherlands, in detail. FIG. 1 illustrates the atomizer which has been described in this literature. The atomizer comprises an oscillator 3 having a pair of interdigital electrodes 5 and 5 on its surface for generating surface acoustic waves, a cover 4 arranged on the oscillating surface side of the oscillator 3, and a tube 1. A liquid 2 to be atomized passes through the tube 1 as shown by arrow A, to be supplied into a clearance between the oscillator 3 and the cover 4. The liquid 2 flowing out from the clearance between the oscillator 3 and the cover 4 is atomized and sprayed by surface acoustic wave vibration.

In the atomizer shown in FIG. 1, various problems arise when the liquid supply quantity and the atomization quantity are unbalanced. If the liquid supply quantity is excessive, an overflow takes place and the atomization may stop. If the liquid supply quantity is insufficient, on the other hand, the atomization becomes so intermittent that continuous and smooth atomization cannot be attained. Further, high electric energy is required for atomizing and spraying the liquid with only vibration of surface acoustic waves, and it is difficult to perform a desired operation with driving by a battery of small power.

DISCLOSURE OF THE INVENTION

An object of the present invention is to provide an atomizer and an atomizing method which can keep the balance between a liquid supply quantity and an atomization quantity excellent and perform stable atomization.

Another object of the present invention is to make it possible to perform stable atomization with small power of a battery or the like.

Still another object of the present invention is to make it possible to perform efficient atomization and spraying.

The atomizer according to the present invention comprises an oscillator generating surface acoustic waves, a porous thin plate having a number of through holes arranged on the oscillating surface of the oscillator with a small clearance, and means for supplying a liquid into the small clearance part between the oscillator and the porous thin plate. The liquid in the small clearance part is atomized by surface acoustic wave vibration propagated by the oscillator, and sprayed through the through holes of the porous thin plate.

According to the aforementioned invention, vibration by the surface acoustic waves is transmitted to the porous thin plate through the liquid in the small clearance part. Due to vibration of the porous thin plate, a small quantity of liquid penetrating into the through holes is atomized and sprayed. The atomizer shown in FIG. 1 is adapted to directly atomize and spray the liquid on the oscillator by vibration of the surface acoustic waves, and hence high electric energy is required. In the atomizing method according to the present invention, on the other hand, it becomes possible to perform atomization by battery driving with small power of about 2 W which is not more than $\frac{1}{10}$ as compared with the apparatus shown in FIG. 1.

The porous thin plate has a number of through holes. As the material for the porous thin plate, ceramics of a hard material with small damping of amplitude by absorption of vibration is preferable. The ceramics is excellent in corrosion resistance, and the safety for the human body is also confirmed. Therefore, in a nebulizer atomizing various types of chemical solutions employed for asthma cure, for example, a porous thin plate (mesh) of ceramics is optimum.

In a preferred embodiment, the atomizer comprises a holder holding both of the oscillator and the porous thin plate with a small clearance. Due to provision of such a holder, the clearance between the oscillator and the porous thin plate is regularly maintained constant.

In one embodiment, the liquid supply means for supplying the liquid into the small clearance part between the oscillator and the porous thin plate includes a liquid container storing the liquid to be atomized. The liquid in the liquid container is aspirated into the small clearance part by vibration by the surface acoustic waves, or by capillarity. According to this embodiment, the liquid is continuously automatically supplied into the small clearance part by the vibration by the surface acoustic waves and/or capillarity by surface tension also after the liquid in the small clearance part is atomized, whereby the balance between the supply quantity of the liquid and the atomization quantity can be kept excellent. Further, it requires no means for forcibly delivering the liquid into the small clearance in particular, whereby miniaturization of the atomizer can be implemented.

In order to efficiently aspirate the liquid from the liquid container into the small clearance part by vibration by surface acoustic waves and/or capillarity by surface tension, the space between the oscillator and the porous thin plate is preferably rendered to gradually enlarge as approaching the liquid container.

The oscillator has a propagation part in which the surface acoustic waves are to be propagated, and a non-propagation part where no surface acoustic waves are propagated. In one preferred embodiment, the small clearance part between the oscillator and the porous thin plate extends over the propagation part and the non-propagation part. In order to aspirate the liquid in the liquid container into the small clearance part by vibration by surface acoustic waves and/or capillarity, the small clearance part on the non-propagation part is dipped in the liquid in the liquid container. In this structure, a region vibrating by the surface acoustic waves is not dipped in the liquid, whereby the load of the vibration does not enlarge and no remarkable reduction of the vibrational amplitude takes place. Therefore, the power of spraying and the atomization efficiency are maintained excellent.

In another embodiment, the liquid supply means of the atomizer comprises a liquid container storing the liquid to be atomized, liquid delivery means for forcibly delivering the liquid in the liquid container into the small clearance part at need, liquid detection means for detecting presence/absence of the liquid in the small clearance part, and control means for controlling the operation of the liquid delivery means in response to a signal from the liquid detection means. This embodiment is adapted to perform supply of the liquid into the small clearance part in response to the detection result of presence/absence of the liquid in the small clearance part, whereby excellent balance can be kept between the supply quantity of the liquid and the atomization quantity. The liquid detection means comprises a first electrode and a second electrode arranged on the oscillating surface of the oscillator in the small clearance part with a space, for example, and detects presence/absence of the liquid by capacitance change between both electrodes, for example.

The atomizing method according to the present invention comprises a step of arranging a porous thin plate having a number of through holes on the oscillating surface of an oscillator generating surface acoustic waves with a small clearance, a step of guiding a liquid into the small clearance part, and a step of atomizing the liquid in the small clearance part by surface acoustic wave vibration propagated by the oscillator and spraying the same through the through holes of the porous thin plate. In one embodiment, the liquid to be atomized is aspirated into the small clearance part from the liquid container storing the liquid by vibration by surface acoustic waves, or by capillarity. In another embodiment, the liquid to be atomized is forcibly delivered from the liquid container storing the liquid into the small clearance part by driving means.

The aforementioned objects and other features as well as advantages of the present invention will become further obvious from the following detailed description made with reference to the drawings.

BEST MODES FOR CARRYING OUT THE INVENTION

Figure 1:
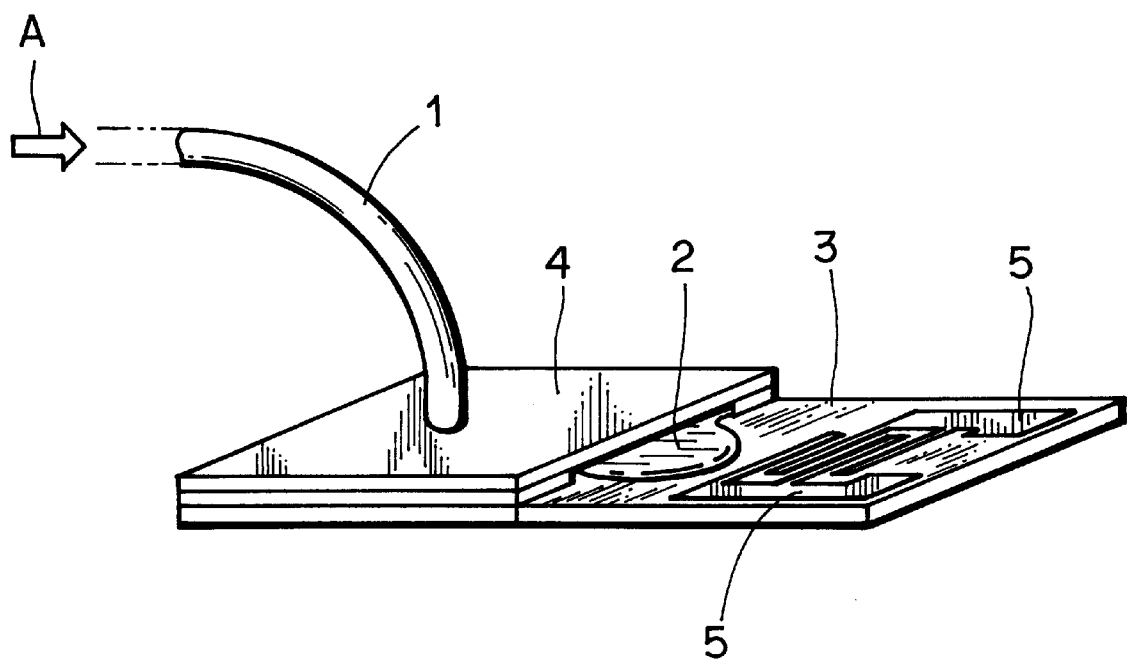
FIG. 1 is a perspective view showing a conventional atomizer employing an oscillator generating surface acoustic waves.
Figure 2:
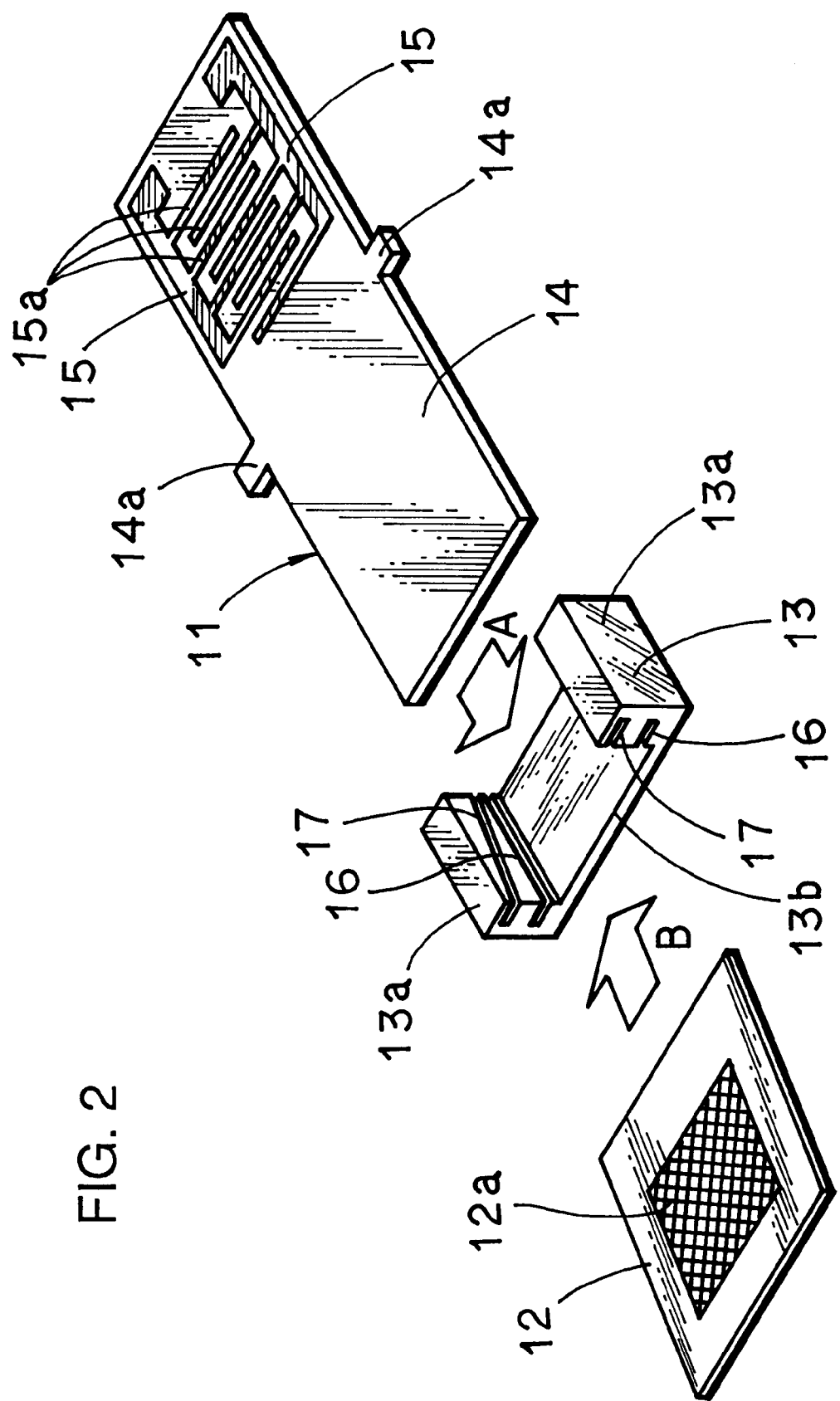
FIG. 2 is an exploded perspective view of an embodiment according to the present invention.
Figure 3:
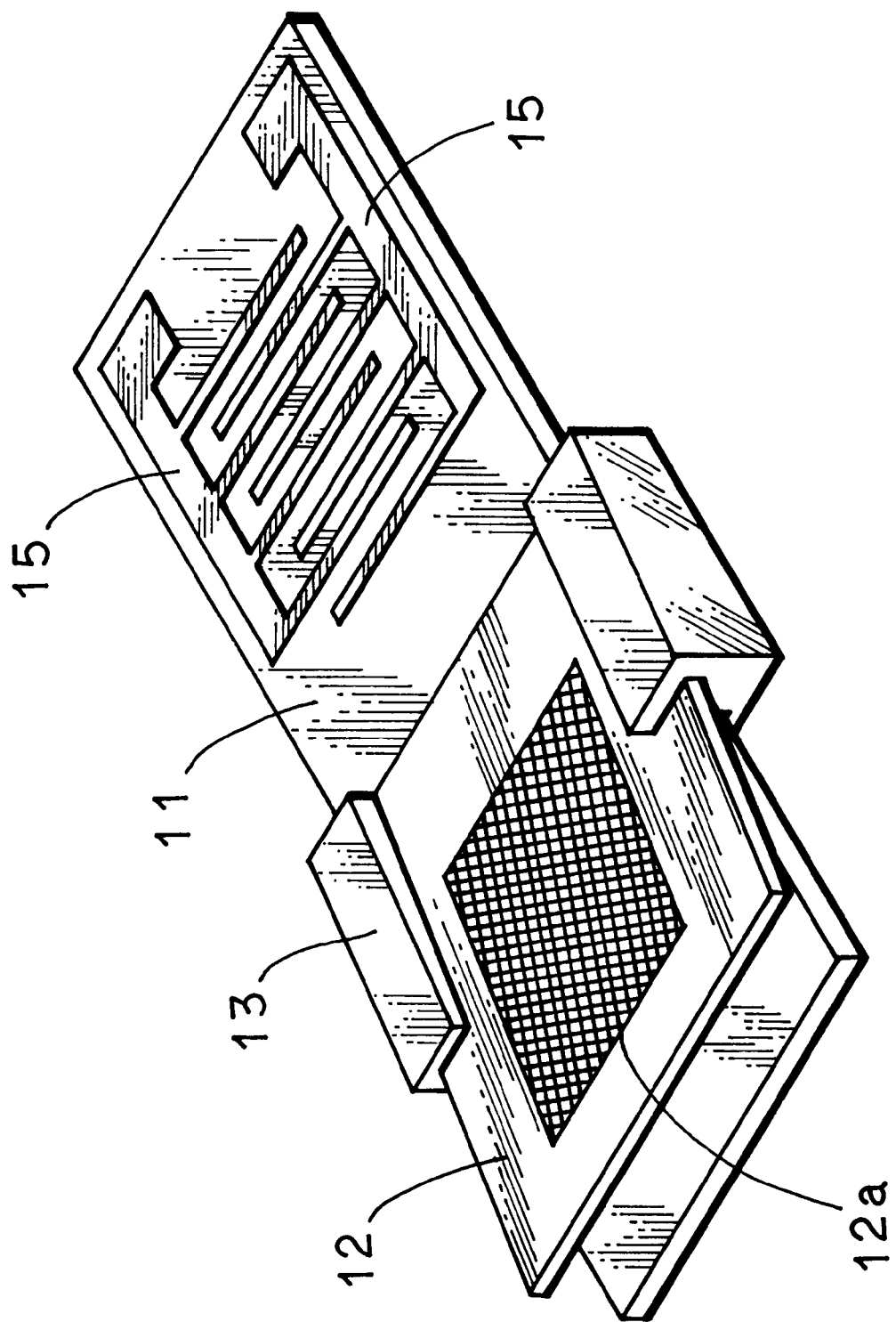
FIG. 3 is a perspective view of the embodiment of the present invention.
Figure 4:
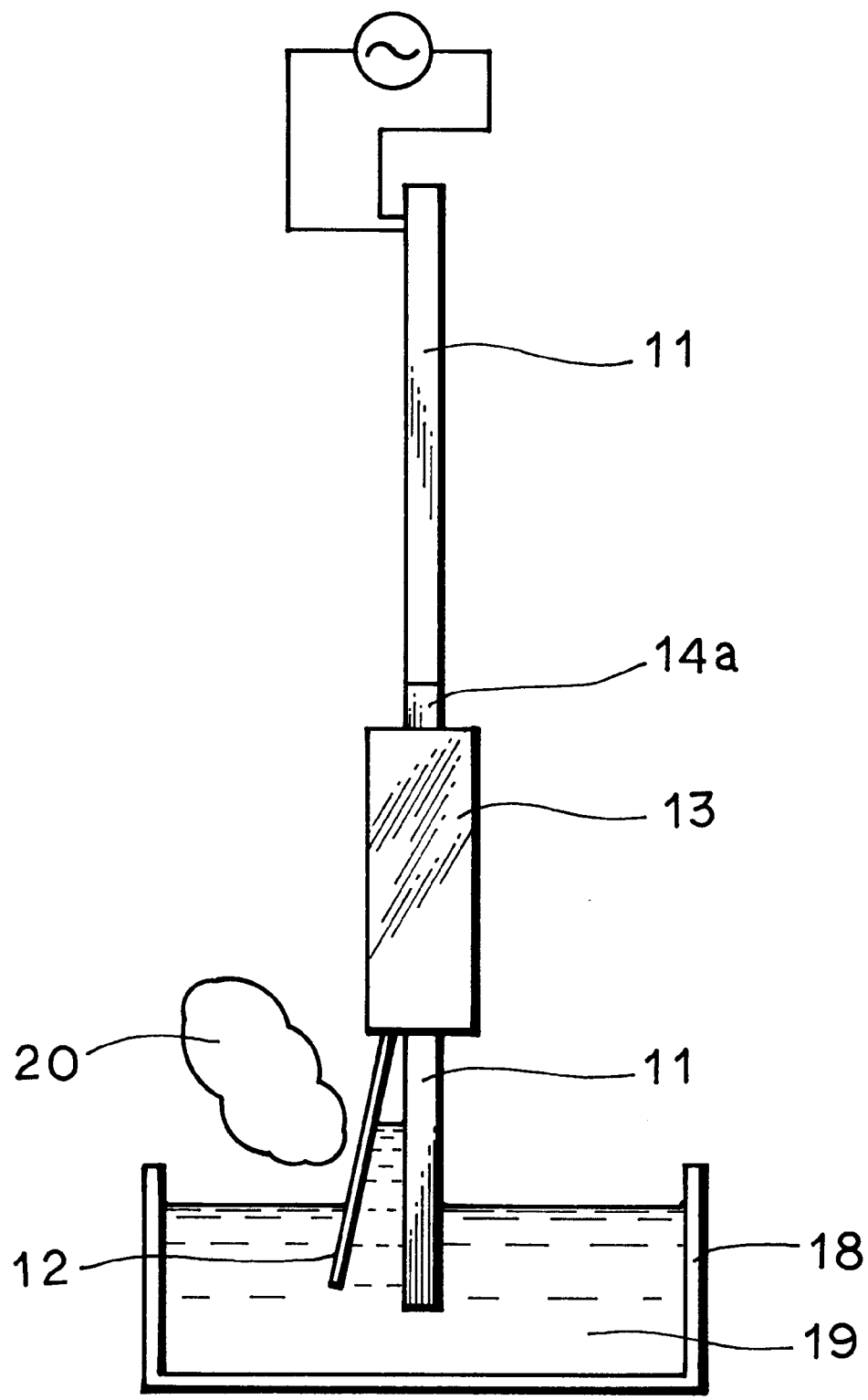
FIG. 4 is a diagram for illustrating a used state of the embodiment of the present invention.

With reference to FIG. 2, FIG. 3 and FIG. 4, an embodiment of the present invention is described.

An atomizer comprises an oscillator 11 generating surface acoustic waves, a thin plate 12 having a mesh 12a substantially at its center, and a holder 13.

The oscillator 11 includes a rectangular substrate 14 prepared from lithium niobate ($LiNbO_3$), for example, and a pair of interdigital electrodes 15 and 15 formed on a surface of this substrate 14. Comb-tooth parts 15a of the pair of interdigital electrodes 15 and 15 are arranged to be alternately positioned along the longitudinal direction of the substrate 14. Surface acoustic waves are generated when a high-frequency voltage is applied between the pair of interdigital electrodes 15 and 15. These surface acoustic waves propagate along the longitudinal direction of the oscillator 11. The substrate 14 of the oscillator 11 has positioning projections 14a and 14a on its side portions.

The substantially quadrilateral thin plate 12 includes the mesh 12a forming a number of through holes. Each hole of the mesh 12a is set at a sufficiently larger diameter than the diameters of atomized grains generated by vibration.

Ceramics is preferable as the material for the mesh 12a. The ceramics does not much absorb vibration, and hence damping of amplitude is small. Further, the ceramics is excellent in corrosion resistance, and the safety for the human body is also confirmed.

As to the holder 13, the shape seen head-on is substantially U-shaped, and the shape seen from above is substantially rectangular, as illustrated. The holder 13 has a pair of side wall parts 13a and 13a, and grooves 16 and 17 are formed on inner wall surfaces thereof. The grooves 16, which are adapted to receive and hold the oscillator 11, extend substantially in parallel with respect to a bottom wall part 13b of the holder 13. The grooves 17 are adapted to receive and hold the thin plate 12 having the mesh. The grooves 17 are formed at an angle with respect to the bottom wall part 13b of the holder 13, and hence the spaces between the grooves 17 and the grooves 16 are not constant. The spaces between these grooves are rendered to gradually enlarge toward the forward ends. As dimensional illustration, the maximum spaces between the grooves 17 and the grooves 17 on the forward ends are rendered to be about 1 (1 mm), assuming that the lengths of the grooves 16 are 10 (10 mm), for example.

In case of manufacturing the atomizer by assembling the oscillator 11, the thin plate 12 having the mesh and the holder 13 with each other, the forward end of the substrate 14 of the oscillator 11 is first moved in the direction shown by arrow A and fitted in the grooves 16 of the holder 13. The movement of the oscillator 11 is performed until the positioning projections 14a come into contact with the holder 13. Then, the thin plate 12 having the mesh is moved in the direction shown by arrow B and fitted in the grooves 17 of the holder 13. Thus, the atomizer shown in FIG. 3 is obtained. A small clearance is formed between the oscillating surface of the oscillator held by the holder 13 and the thin plate 12 having the mesh. The space between the oscillator 11 and the thin plate 12 is rendered to gradually enlarge toward the forward end.

With reference to FIG. 4, an operation of the atomizer in use is described.

A liquid 19 to be atomized is stored in a liquid container 18. The forward end of the oscillator 11 and/or the forward end of the thin plate 12 having the mesh is dipped in the liquid in the liquid container 18. Namely, the small clearance part between the oscillator 11 and the thin plate 12 is dipped in the liquid. When the oscillator 11 is driven in this state, surface acoustic waves are generated from the comb-tooth parts 15a of the oscillator 11, and these surface acoustic waves propagate on the oscillating surface of the oscillator 11 to reach the liquid surface of the liquid container 18. Due to vibration by these surface acoustic waves and capillarity by surface tension, the liquid 19 is aspirated into the small clearance part between the oscillator 11 and the thin plate 12. The quantity of the liquid in the small clearance part is small and proper, so that the liquid can be sufficiently atomized by the vibrational amplitude of surface waves driven with small power. The vibration on the oscillating surface of the oscillator 11 is transmitted to the mesh 12a of the thin plate 12 through the liquid in the small clearance part. Due to vibration of the mesh 12, the small quantity of liquid penetrating into the hole parts are atomized and sprayed.

Figure 5:
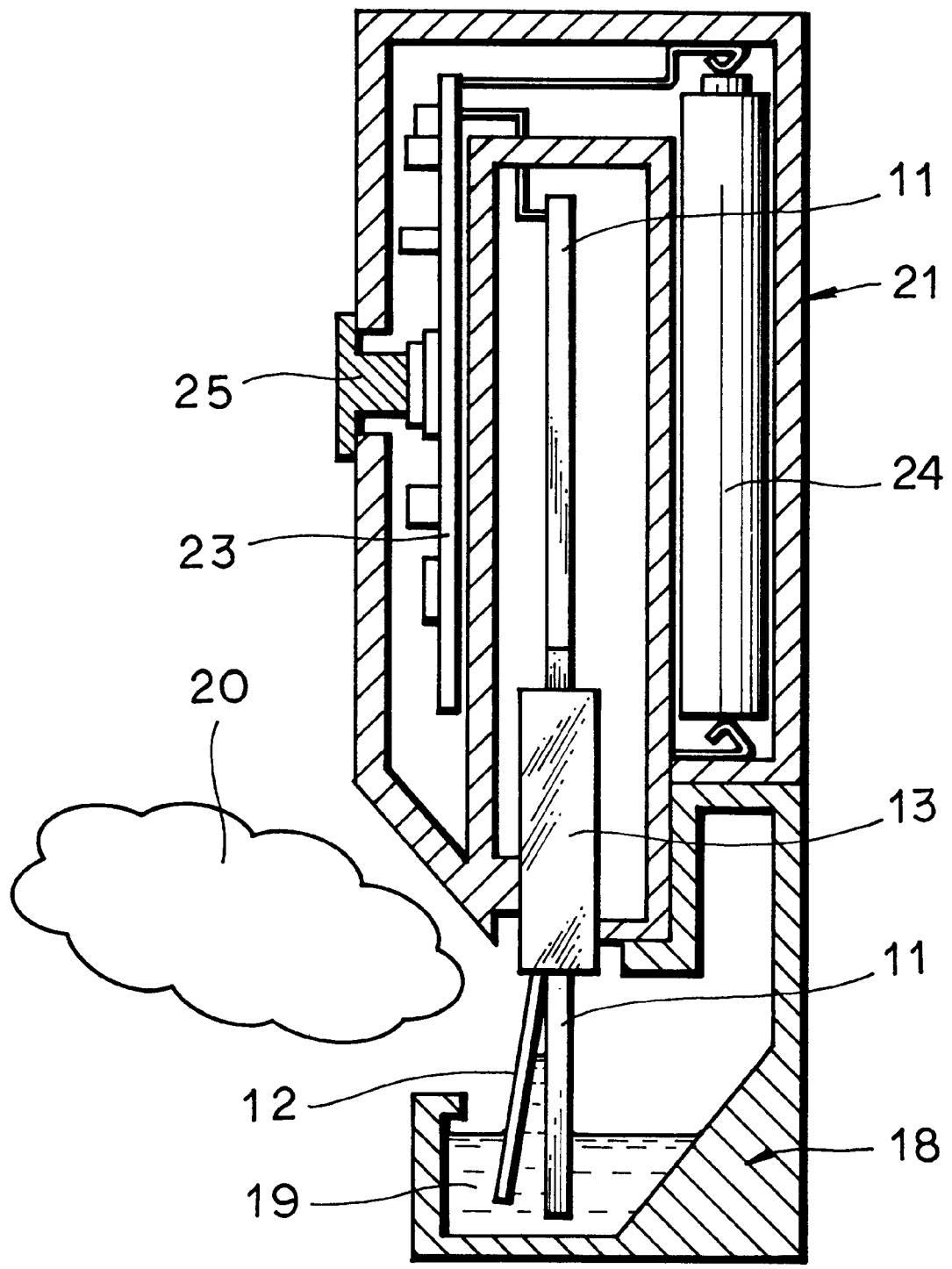
FIG. 5 is a diagram showing an exemplary aspirator into which the atomizer is assembled.

FIG. 5 is a sectional view of an aspirator into which the atomizer shown in FIG. 2 to FIG. 4 is assembled. The aspirator comprises a body case 21, and a chemical solution bottle 18. In the body case 21, a circuit board 23 carrying a circuit for driving the oscillator 11, a battery 24 and a power supply switch 25 are stored in addition to the atomizer consisting of the oscillator 11, the thin plate 12 having the mesh and the holder 13. The chemical solution bottle 18 stores a chemical solution 19 when in use, and is mounted on a lower portion of the body case 21. As illustrated, lower end portions of the oscillator 11 and the thin plate 12 having the mesh are dipped in the chemical solution 19. The small clearance part between the oscillator 11 and the thin plate 12 having the mesh is filled with the liquid, and hence the liquid in the small clearance part is atomized in the holes of the mesh 12a of the thin plate 12 and sprayed to the exterior by vibration of the surface acoustic waves when the power supply switch 25 is turned on. Reference numeral 20 denotes sprayed mist.

According to the aforementioned embodiment, the small quantity of liquid penetrating into the holes of the mesh 12a of the thin plate 12 is atomized and sprayed by surface acoustic wave vibration, whereby stable atomization can be performed also by driving with the battery. Further, supply of the liquid into the small clearance part is automatically performed by vibration by surface acoustic waves and/or surface tension, whereby means for forcibly delivering the liquid is not particularly required, and hence a miniature atomizer is obtained. Further, the liquid is supplied from the liquid container in response to atomization, whereby the balance between the supply quantity of the liquid and the atomization quantity can be kept excellent.

While the thin plate 12 having the mesh has been employed as the porous thin plate having a number of through holes, the porous thin plate is not restricted to such a mesh, but a flat thin plate formed with a number of through holes may be employed.

Figure 6:
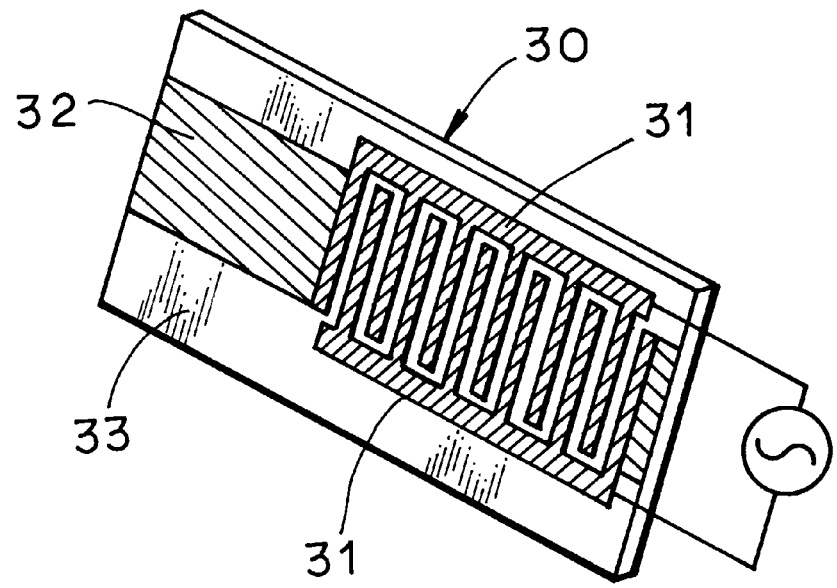
FIG. 6 is a perspective view showing an oscillator generating surface acoustic waves.

FIG. 6 illustrates an oscillator 30 having a pair of interdigital electrodes 31 and 31. Surface acoustic waves generated by application of a voltage between the pair of interdigital electrodes 31 and 31 are propagated in the longitudinal direction of the oscillator 30 in the width of a region where comb-tooth parts of the interdigital electrodes overlap with each other. Referring to FIG. 6, a region 32 shown by slant lines is a propagation part where the surface acoustic waves are propagated, and the remaining region 33 is a non-propagation part where no surface acoustic waves are propagated. In such a state that the forward end portion of the oscillator 30 is not dipped in a liquid, the surface acoustic waves are reflected by an end surface of the oscillator 30 and interfere with traveling waves, standing waves are generated and the vibrational amplitude increases. If the end surface of the oscillator 30 is dipped in the liquid similarly to the aforementioned embodiment, however, there is the possibility that the load of the vibration increases, the surface acoustic waves are diffused in the liquid, and increase of the vibrational amplitude by standing waves cannot be expected. In other words, there is the possibility that the power of atomization or atomization efficiency reduces, if the portion in the oscillator 30 dipped in the liquid is the surface acoustic wave propagation direction side.

Figure 7:
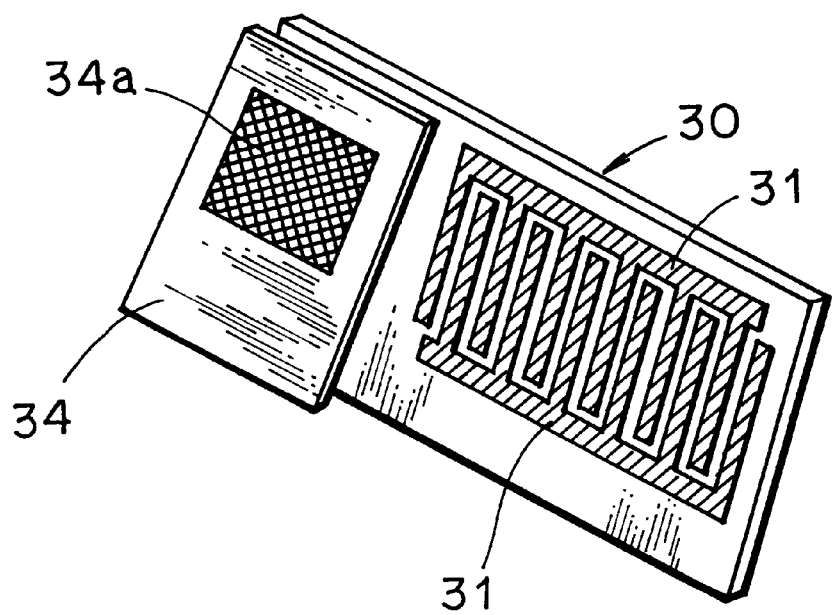
FIG. 7 is a perspective view showing another embodiment according to the present invention.
Figure 8:
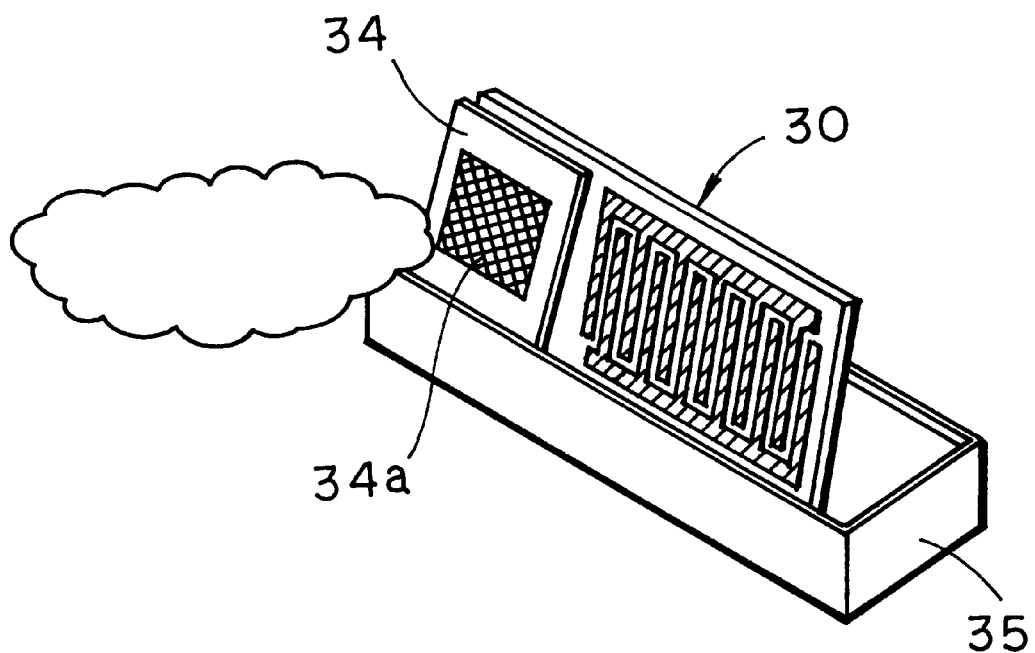
FIG. 8 is a diagram for illustrating a used state of the aforementioned another embodiment.
Figure 9:
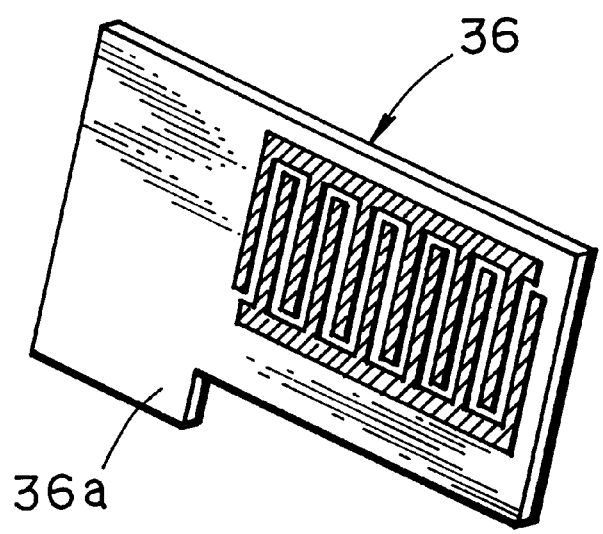
FIG. 9 is a perspective view showing an oscillator having a projecting non-propagation part.

In an embodiment shown in FIG. 7 to FIG. 9, therefore, a non-propagation part where no surface acoustic waves are propagated in an oscillator 30 is dipped in a liquid. Concretely, a thin plate 34 having a mesh 34a faces both of a propagation part and the non-propagation part of the oscillator 30, to form a small clearance part. The space between the oscillator 30 and the thin plate 34 having the mesh 34a is rendered to gradually enlarge as approaching a liquid container.

FIG. 8 shows such a state that the propagation part positioned on a side portion of the oscillator 30 and the forward end of the thin plate 34 having the mesh are dipped in the liquid in the liquid container 35. In this embodiment, the propagation part where the surface acoustic waves are propagated is not dipped in the liquid, whereby the vibrational load does not increase, and no reduction of the vibrational amplitude takes place either. Thus, improvement of the power of atomization or the atomization efficiency is expected.

FIG. 9 illustrates another example of an oscillator 36 generating surface acoustic waves. The illustrated oscillator 36 has a projecting part 36a swelling its outer edge in a region where no surface acoustic waves are propagated. This projecting part 36a is dipped in a liquid in a liquid container.

In the embodiments shown in FIG. 2 to FIG. 9, supply of the liquid into the small clearance part between the oscillator and the porous thin plate has been automatically performed by vibration by the surface acoustic waves, or by capillarity by surface tension. On the other hand, an embodiment shown in FIG. 10 to FIG. 13 forcibly performs supply of a liquid in a small clearance part by driving means. In this case, it is necessary to keep excellent balance between the supply quantity of the liquid and an atomization quantity.

Figure 11:
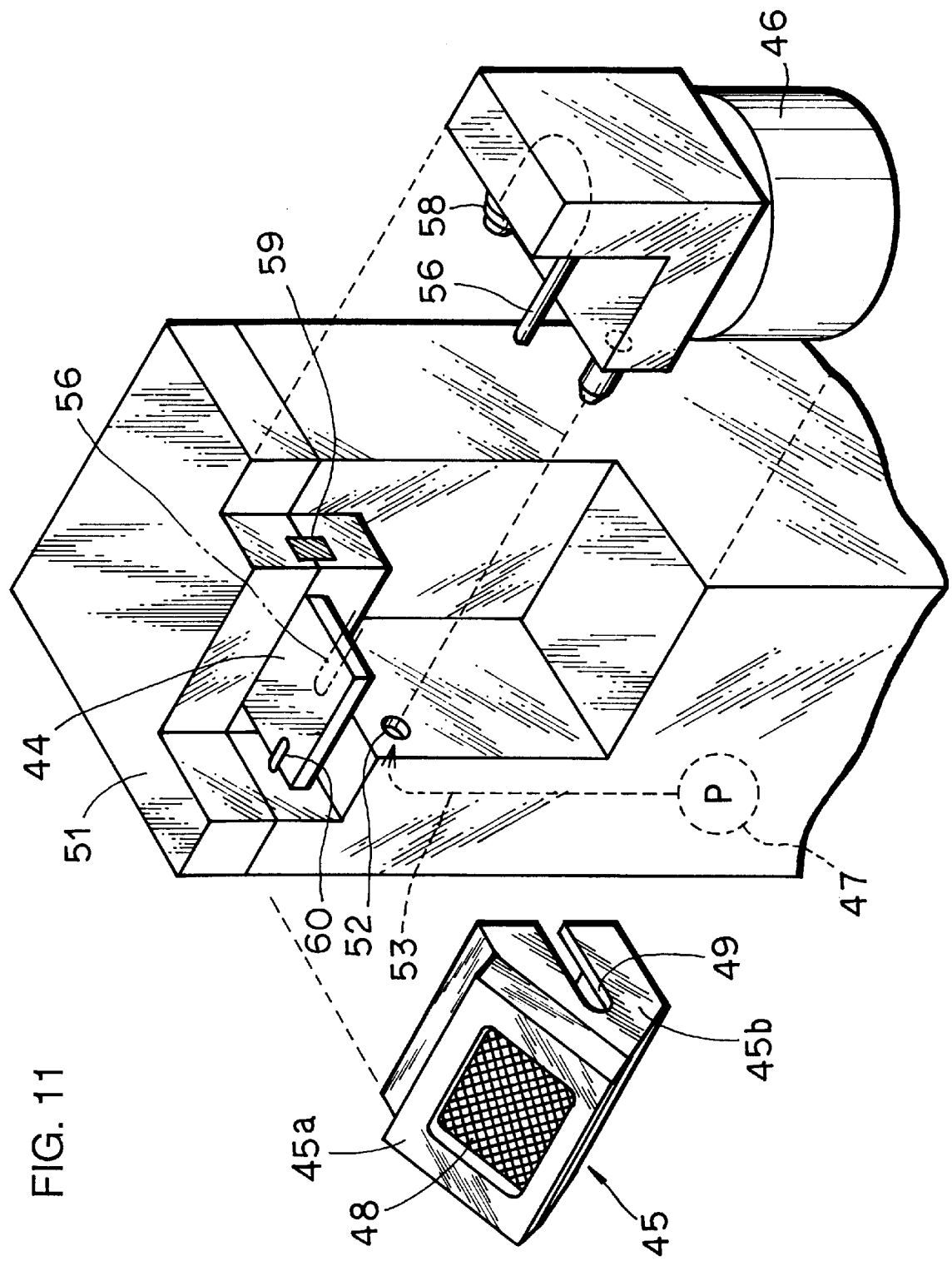
FIG. 11 is an exploded perspective view of an atomizer.

Referring to FIG. 11, an atomizer comprises a body 51 holding an oscillator 44 generating surface acoustic waves, a cap 45 having a mesh which is so mounted on the body 51 as to receive the oscillator 44 in its interior, and a liquid bottle 46 storing a liquid supplied onto the oscillating surface of the oscillator 44.

Figure 12:
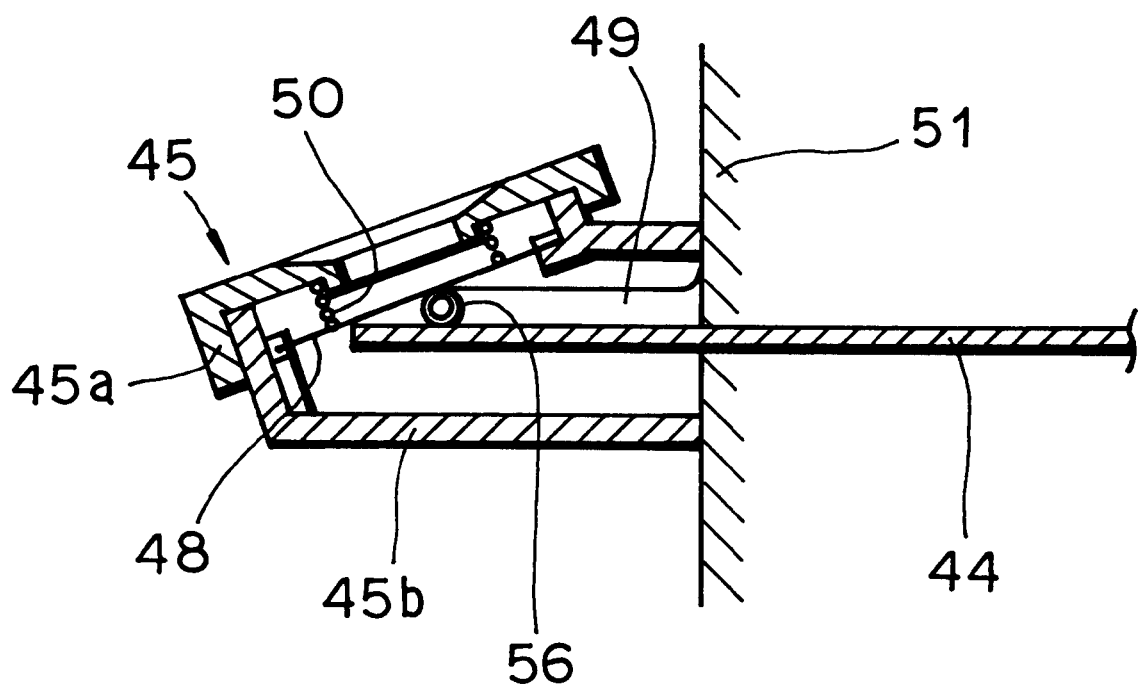
FIG. 12 is a sectional view of a state combining an oscillator and a cap having a porous thin plate with each other.

Referring to FIG. 12, the cap 45 comprises an upper cap 45a having an opening in its center, a lower cap 45b, and a mesh 48 held by elastic repulsive force of a coil spring 50. A slot 49 receiving a projecting pipe 56 of the liquid bottle 46 is formed on a side wall of the lower cap 45b. As obvious from FIG. 12, a small clearance part is formed between the mesh (porous thin plate) 48 and the oscillating surface of the diaphragm 44. The liquid in the liquid bottle 46 is supplied into this small clearance part through the projecting pipe 56.

Figure 13:
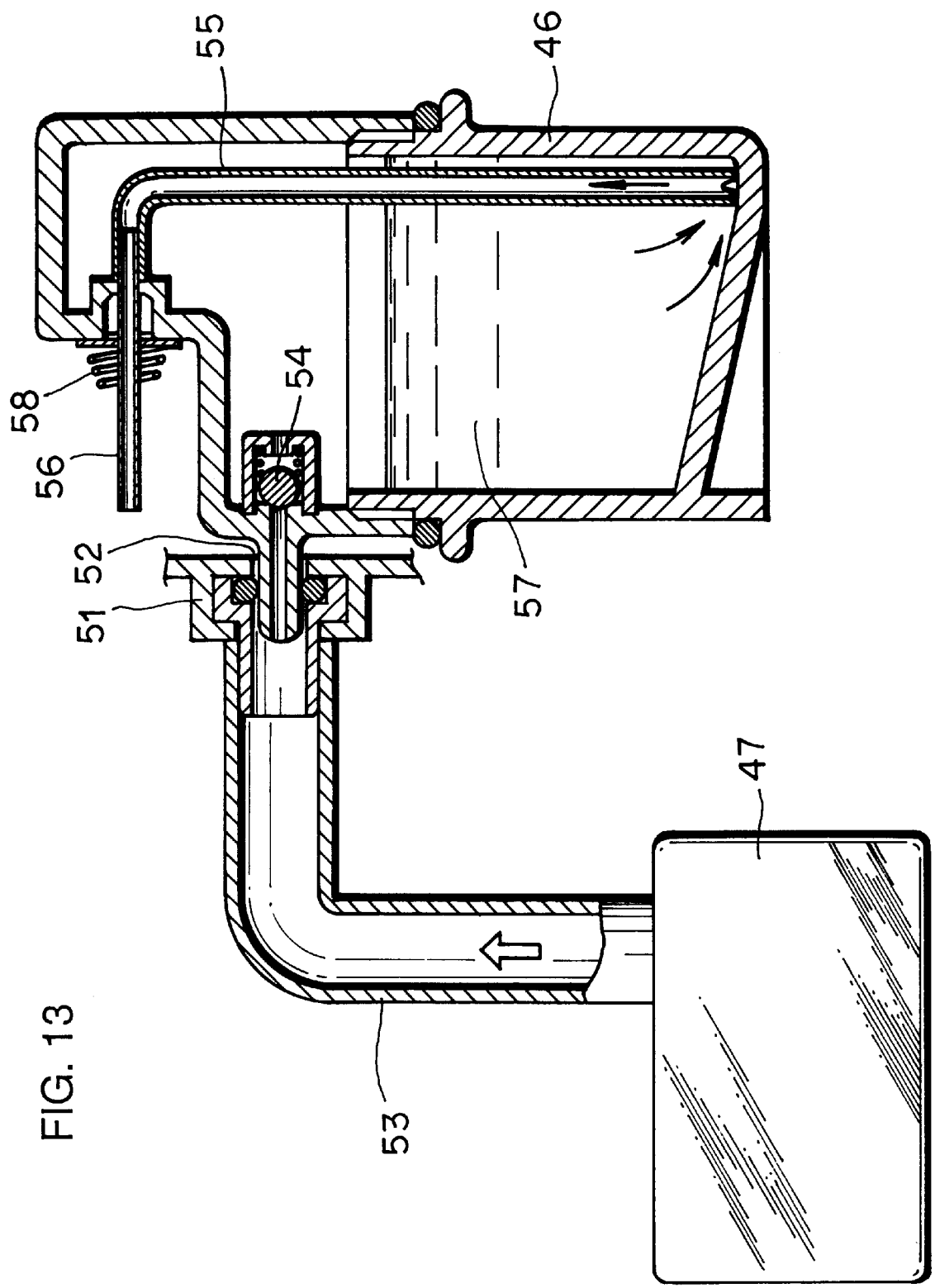
FIG. 13 is a sectional view showing a mechanism for supplying a liquid.

FIG. 13 illustrates a structure related to the liquid bottle 46. The liquid bottle 46 stores a liquid 57 in its interior, while its upper space is closed. High-pressure air delivered by a pressure pump 47 stored in the body 51 is introduced into the upper space of the liquid bottle 46 through a tube 53 and a check valve 54. The pressure in the liquid bottle 46 rises due to this introduction of the high-pressure air, so that the liquid 57 in the liquid bottle 46 is delivered into the small clearance part between the oscillator 44 and the mesh 48 through a tube 55 and the projecting pipe 56.

The atomizer shown in FIG. 10 to FIG. 13 comprises liquid detection means detecting presence/absence of the liquid in the small clearance part between the oscillator 44 and the mesh 48. Concretely, two electrodes are arranged on the oscillating surface of the oscillator 44 in the small clearance part with a space. As to one electrode, its function is executed by the projecting pipe 56. The other electrode 60 projects from the body 51. A space is formed between the projecting pipe 56 (first electrode) and the second electrode 60, and capacitance change between both electrodes results from presence/absence of the liquid in this portion. Presence/absence of the liquid is detected by this capacitance change. The body 51 is provided with an electrode contact 59. The liquid bottle 46 is also provided with an electrode contact 58 for coming into contact with the electrode contact 59. The projecting pipe 56 and the electrode contact 58 are electrically connected with each other.

Figure 10:
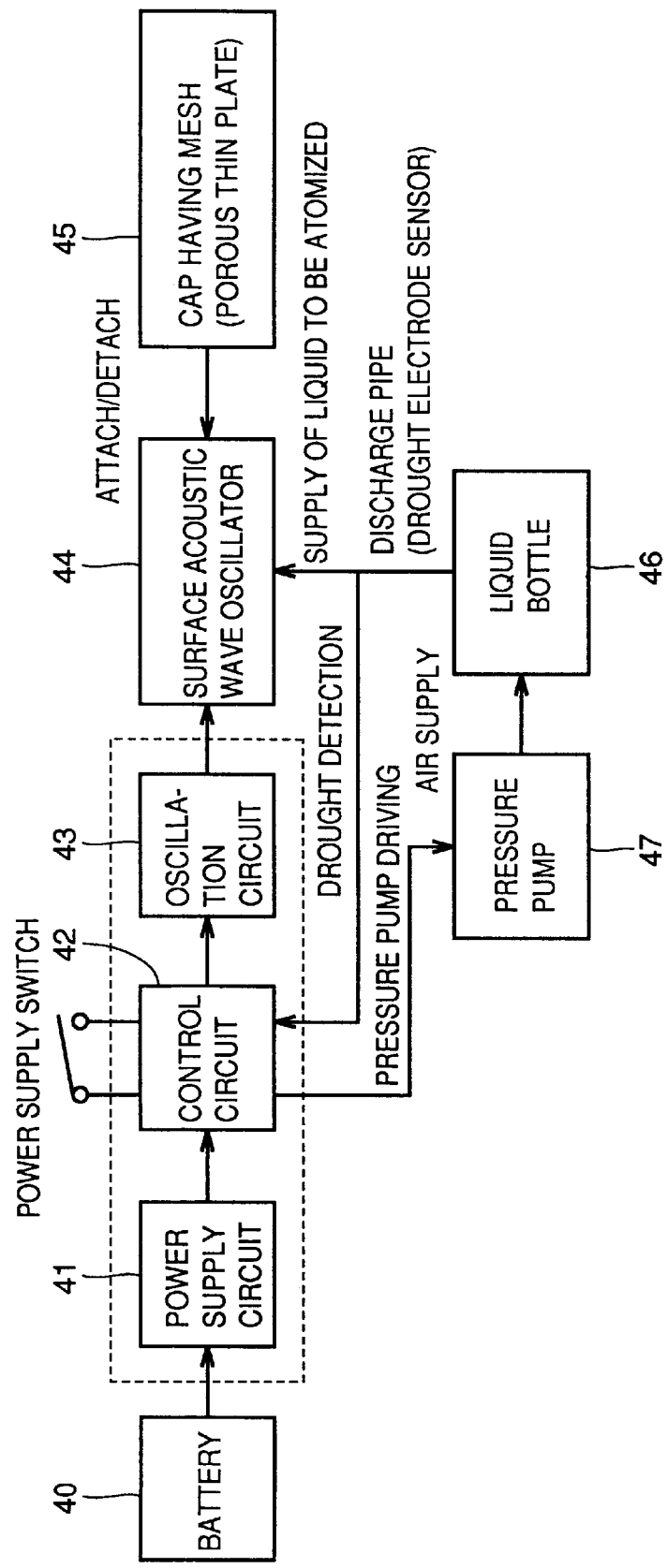
FIG. 10 is a block diagram of still another embodiment according to the present invention.

Ceramics is optimum as the material for the mesh 48 which is a porous thin plate. There is the possibility that dispersion is caused in the atomization quantity due to the sizes of the holes of the mesh etc. Even if such dispersion of the atomization quantity takes place, it is desirable to continuously perform stable atomization. In the embodiment shown in FIG. 10 to FIG. 13, therefore, the liquid detection means for detecting presence/absence of the liquid in the small clearance part is provided, to forcibly deliver the liquid in the liquid bottle 46 into the small clearance part in response to a signal from this liquid detection means. For this control, the atomizer comprises a battery 40, a power supply circuit 41, a control circuit 42, an oscillation circuit 43, the pressure pump 47 and the liquid bottle 46, as shown in FIG. 10. Its operation is performed as follows:

When a proper quantity of liquid is present in the small clearance part between the oscillator 44 and the mesh 48, the pressure pump 47 is not driven. If the liquid in the small clearance part becomes insufficient, on the other hand, the capacitance between the first electrode 56 and the second electrode 60 changes, whereby absence of the liquid is detected. The control circuit 42 drives the pressure pump 47 in response to the detection signal. The high-pressure air delivered from the pressure pump 47 is introduced into the liquid bottle 46, whereby the liquid in the liquid bottle 46 is delivered into the small clearance part between the oscillator 44 and the mesh 48 through the tube 55 and the projecting pipe 56. Vibration of surface acoustic waves propagated on the oscillating surface of the oscillator 44 is transmitted to the mesh 48 through the liquid in the small clearance part, for atomizing a small quantity of liquid penetrating into the holes of the mesh 48 and spraying the same to the exterior. Due to repetition of this operation, the balance between the supply quantity of the liquid and the atomization quantity is kept excellent. This embodiment is adapted to introduce the high-pressure air into the liquid bottle 46 for delivering the liquid, whereby the liquid in the liquid bottle 46 can be sufficiently consumed. When a proper quantity of liquid is present in the small clearance part, the pressure pump 47 is not driven, and hence supply of the liquid into the small clearance part is intermittently performed.

The electrode sensors 56 and 60 for detecting drought must be periodically detached and washed, for preventing malfunctions. The illustrated embodiment employs the projecting pipe 56 for serving also as one electrode sensor, in order to reduce the number of the parts and simplify the structure.

While some embodiments of the present invention have been illustratively described with reference to the drawings, the present invention is not restricted to the illustrated embodiments, but various corrections and modifications are possible within the uniform range.

Industrial Availability

The present invention can be advantageously applied to an aspirator for atomizing a chemical solution effective for asthma cure, pulmonary disease cure or the like.

We claim:

1. An atomizer comprising:

an oscillator generating surface acoustic waves;

a porous thin plate having a number of through holes being arranged on the oscillating surface of said oscillator with a small clearance space between said oscillator and said porous thin plate; and means for supplying a liquid into said small clearance space between said oscillator and said porous thin plate, and means for atomizing the liquid in said small clearance space by surface acoustic wave vibration propagated by said oscillator and spraying the same through the through holes of said porous thin plate.

2. The atomizer in accordance with claim 1, wherein said porous thin plate is a mesh.

3. The atomizer in accordance with claim 1, wherein said porous thin plate is made of ceramics.

4. The atomizer in accordance with claim 1, further comprising a holder (13) holding both of said oscillator and said porous thin plate with a small clearance.

5. The atomizer in accordance with claim 1, wherein said liquid supply means includes a liquid container (18, 35) storing the liquid to be atomized, the liquid in said liquid container being aspirated into said small clearance space by vibration by the surface acoustic waves, or by capillarity.

6. The atomizer in accordance with claim 5, wherein the space between said oscillator and said porous thin plate is rendered to gradually enlarge as approaching said liquid container.

7. The atomizer in accordance with claim 5, wherein said oscillator has a propagation part (32) where the surface acoustic waves are propagated and a non-propagation part (33) where no surface acoustic waves are propagated, said small clearance space extends over said propagation part and said non-propagation part, and said non-propagation part is dipped in the liquid in said liquid container.

8. The atomizer in accordance with claim 7, wherein said oscillator has a projecting part (36a) swelling its outer edge in a region where no surface acoustic waves are propagated, said projecting part being dipped in the liquid in said liquid container.

9. The atomizer in accordance with claim 1, wherein said supply means comprises:

a liquid container (46) storing the liquid to be atomized, liquid delivery means (47) forcibly delivering the liquid in said liquid container into said small clearance space at need, liquid detection means (56, 60) detecting presence/absence of the liquid in said small clearance space, and control means (42) controlling the operation of said liquid delivery means in response to a signal from said liquid detection means.

10. The atomizer in accordance with claim 9, wherein said liquid detection means comprises a first electrode (56) and a second electrode (60) being arranged on the oscillating surface of said oscillator in said small clearance space with a space, for detecting presence/absence of the liquid by capacitance change between both electrodes.

11. The atomizer in accordance with claim 10, wherein said liquid delivery means has a discharge pipe (56) having a liquid discharge port in said small clearance space, said discharge pipe being used as said first electrode.

12. An atomizing method comprising:

arranging a porous thin plate having a number of through holes on the oscillating surface of an oscillator generating surface acoustic waves with a small clearance space between said oscillator and said porous thin plate;

guiding a liquid into said small clearance space, and atomizing the liquid in said small clearance space by surface acoustic wave vibration propagated by the oscillator and spraying the same through the through holes of said porous thin plate, wherein said small clearance space is not constant in width.

13. The atomizing method in accordance with claim 12, wherein the liquid to be atomized is aspirated into said small clearance space from a liquid container storing the liquid by vibration by surface acoustic waves, or by capillarity.

14. The atomizing method in accordance with claim 12, wherein the liquid to be atomized is forcibly delivered into the small clearance space from a liquid container storing the liquid by driving means.

* * * * *